United States Patent [19]

Kössler et al.

[11] 3,981,182

[45] Sept. 21, 1976

[54] FLOW-THROUGH CAPILLARY VISCOMETER

[76] Inventors: Ivo Kössler, Hradesinska 59, Prague, Czechoslovakia, 101 00; Karel Habr, v Houstce 5/1032, Brandys n.L., Czechoslovakia

[22] Filed: July 11, 1975

[21] Appl. No.: 596,024

[30] Foreign Application Priority Data

July 16, 1974 Czechoslovakia............. 5072-74

[52] U.S. Cl. ............................................. 73/55
[51] Int. Cl.². ...................................... G01N 11/06
[58] Field of Search ........................................ 73/55

[56] References Cited

UNITED STATES PATENTS

| 2,048,305 | 7/1936 | Ubbelohde | 73/55 |
| 2,095,282 | 10/1937 | Payne | 73/55 |
| 2,095,324 | 10/1937 | FitzSimons | 73/55 |
| 2,343,061 | 2/1944 | Irany | 73/55 |
| 3,559,463 | 2/1971 | Tovrog et al. | 73/55 |
| 3,864,962 | 2/1975 | Stark et al. | 73/55 |

FOREIGN PATENTS OR APPLICATIONS 713,990  11/1941  Germany ........................ 73/55

*Primary Examiner*—Richard C. Queisser
*Assistant Examiner*—Joseph W. Roskos
*Attorney, Agent, or Firm*—Lawrence Rosen; E. Janet Berry

[57]. ABSTRACT

A capillary viscometer for measurement of viscosity of liquids conprising, in addition to the usual capillary tube and measuring bulb, a filling tube leading to an inlet bulb with a tube opening between the capillary tube and the measuring bulb. The inlet bulb is connected by an overflow tube with an outlet tube of the viscometer situated below the measuring capillary tube. The inlet bulb is also connected by a subsidiary capillary tube with the overflow tube. When determining the viscosity, the liquid is poured into the filling tube, flows through it into the inlet bulb; the excessive liquid flows out through the overflow tube. At the same time the measuring bulb is filled from the bottom by the liquid flowing from the inlet bulb. The first portion of this liquid washes the measuring bulb from the preceding sample, and the contaminated portion of the liquid flows out through the overflow tube. Simultaneously a small quantity of the liquid flows through and washes the measuring capillary tube. The pure portion of the liquid then flows freely through the measuring capillary tube and the corresponding time of flow is determined. All operations, i.e., the filling of the viscometer, the filling of the measuring bulb, the flow of liquid through the capillary tube, and washing of the viscometer for the next measurement are performed in one single step. The viscometer may be equipped with a reservoir for tempering of the liquid positioned above the filling tube or with a siphon positioned above the filling tube.

7 Claims, 5 Drawing Figures

FLOW-THROUGH CAPILLARY VISCOMETER

Flow-through capillary viscometer where the tubings for the liquid flow are arranged in such a way that the process is simplified, the necessary measuring time is shortened and the possibility of error through the improper introduction of the liquid is eliminated.

The capillary flow-through viscometers used presently consist of a measuring bulb situated above and connected to a measuring capillary tube by means of a connection tube. The measuring bulb is filled with the liquid by a tube which opens into the measuring tube in its upper part. No means is provided for the diversion of a possibly superfluous amount of liquid. In case that a small quantity of liquid flows into the viscometer during the measurement, e.g. a drop from the siphon which doses the liquid into viscometer, the results are distorted. The presently known flow-through viscometers do not form a single unit with the dosing siphon and they are equipped with no device for a defined tempering of the liquid before the measurement.

The present invention relates to a flow-through capillary viscometer with the measuring bulb situated above the measuring capillary tube and connected by a tube with the inlet bulb. According to the invention this connecting tube joins the lower part of the inlet bulb with the lower part of the measuring bulb. The inlet bulb may be connected by an air outlet tube with the upper part of the measuring bulb or by an overflow tube with the outlet tube, which is situated below the measuring capillary tube. It can just as well be connected with both tubes, the air-outlet tube as well as the overflow tube. It is an advantage when the lower part of the inlet bulb is inclined downward and connected by a subsidiary capillary tube with the overflow tube. The invention includes two different arrangements for the introduction of the liquid sample, either a siphon or a sample-thermostating chamber. Either shall be incorporated into the flow-through capillary viscometer such as to form one unit. In the outlet of this sample-thermostating chamber a valve is situated, controlled most suitably by an electromagnet.

The siphon or sample-thermostating chamber is situated above the filling tube, and opens into the inlet bulb.

The measuring bulb above the capillary tube is filled from below such that no air bubbles can be formed. This eliminates disturbances in the filling process as well as a possible false recording by the photosensors which are used for the exact determination of the flow-time of the liquid. Air bubbles pose a special obstacle during the filling with liquids of higher viscosity.

Any superfluous liquid leaves the viscometer by the overflow tube without passing through the capillary tube. This overflow tube arrangement allows the dosing into the viscometer by an arbitrary amount of liquid without previous volume determination.

The auxillary capillary tube allows for the use of any type of siphon. Small quantities of liquid entering the device during the measurement pass through the auxillary capillary tube directly into the overflow tube, thereby not affecting the results.

The connection of the siphon with the viscometer gives the possibility of continuous viscosity determination, e.g. in the course of production processes, the principle of determining the viscosity by measuring the flow-time of the liquid through a capillary tube being maintained. When the liquid to be measured is introduced slowly into the siphon, the incorporation of the siphon and viscometer into one unit gives optimum thermostating.

Incorporating the sample-thermostating chamber in the viscometer also enables an automation of the liquid-thermostating under optimum conditions because any transport of the liquid from the separate thermostating bulb into the viscometer is excluded.

In the accompanying drawings five examples of the arrangement of viscometers according to the invention are given.

FIG. 1 shows the arrangement of three tubes: for the filling of the measuring bulb from below, for the overflow of a superfluous quantity of the liquid, and for the outlet of small amounts of the liquid by the subsidiary capillary tube into the overflow tube.

In the FIG. 2 an alternative case with an air-outlet tube opening into the overflow tube is shown.

FIG. 3 shows the incorporation of a siphon with the viscometer, and in FIG. 4 a chamber for liquid-thermostating before the measurement, provided with a valve, is shown.

In FIG. 5 a detail of the viscometer with the tubes for the insertion of the photosensors is drawn.

DETAILED DESCRIPTION OF THE FIGURES

Figure 1:
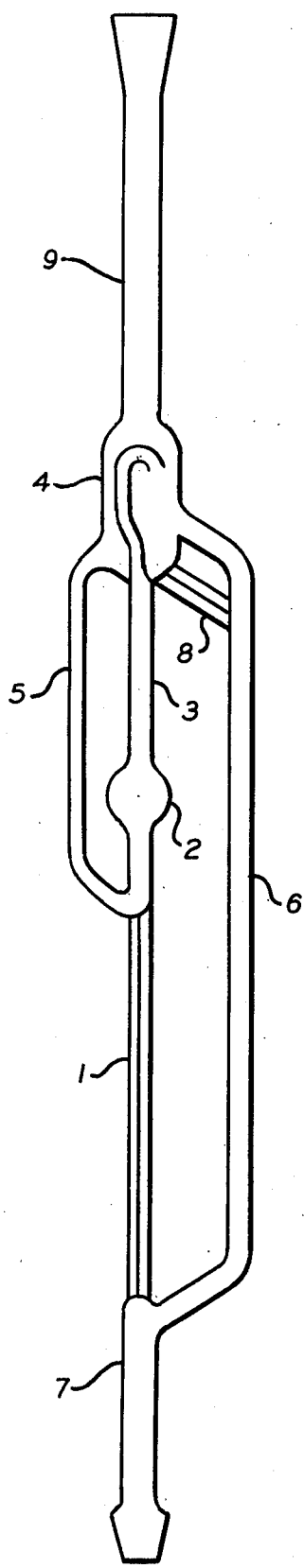

FIG. 1: Above the measuring capillary tube 1 is the measuring bulb 2 with the air-outlet tube 3 which connects the measuring bulb 2 with the inlet bulb 4. The inlet bulb 4 is connected by the connecting tube 5 with the upper part of the measuring capillary tube 1 and by the overflow tube 6 with the outlet tube 7, which is situated below the measuring capillary tube 1. The lower part of the inlet bulb 4 is inclined and connected by the subsidiary capillary tube 8 with the overflow tube 6. The upper part of the inlet bulb 4 is connected with the filling tube 9.

Figure 2:
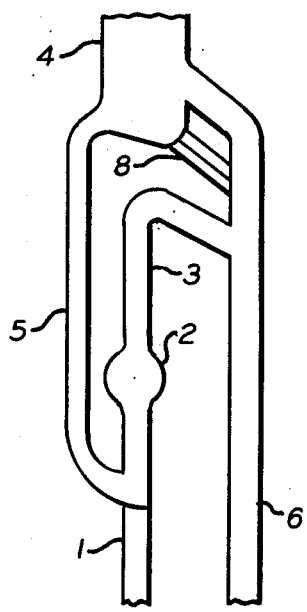

FIG. 2: The measuring bulb 2 is connected by the air-outlet tube 3 with the overflow tube 6.

Figure 3:
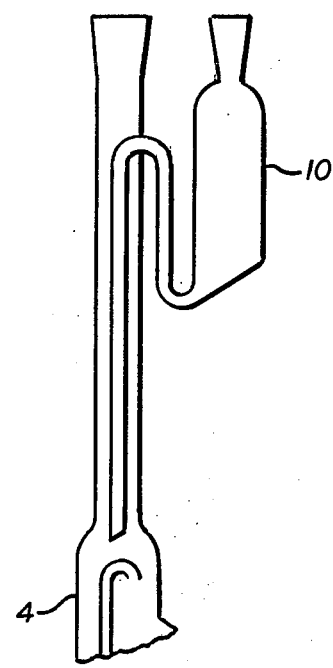

FIG. 3: Above the inlet bulb 4 is a siphon 10, which opens into the inlet bulb 4.

Figure 4:
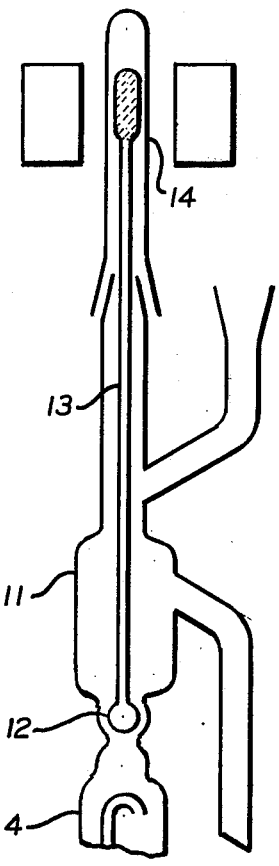

FIG. 4: The sample-thermostating chamber 11 is situated above the inlet bulb 4, which opens into the inlet bulb 4. In the opening of the chamber 11 into the inlet bulb 4 the valve 12 is situated, which is connected with the rod 13 situated in the field of the electromagnet 14.

Figure 5:
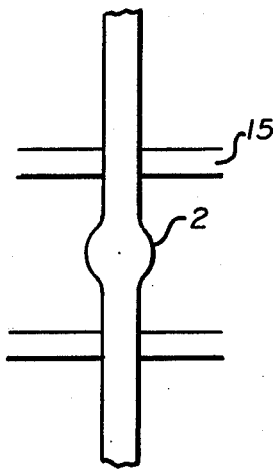

FIG. 5: The tubes connected with the measuring bulb 2 are provided with four small tubes for the insertion of the photosensors.

The filling of the measuring tube 2 is performed through the tubes 9, 4, and 5, the superfluous liquid being let out by the overflow tube 6 into the outlet tube 7. The subsidiary capillary tube 8 drains any small quantities of liquid which may have entered the inlet bulb 4 during the measurement.

The tube 3 is provided either with gauge marks above and below measuring bulb 2 for the optical reading of the passing of the meniscus of the flowing liquid or with photosensors for the automatic measurement or, according to FIG. 5, with tubes for the insertion of the photosensors.

What is claimed is:

1. In a flow-through capillary viscometer comprising an inlet filling tube, an inlet filling bulb, a measuring capillary tube, and a measuring bulb positioned above said measuring capillary tube; the improvement which comprises providing a filling tube joining the lower part of said inlet filling bulb with the lower part of said measuring bulb, and wherein said measuring bulb is connected by an air-outlet tube to said inlet filling bulb or an overflow tube.

2. In the flow-through capillary viscometer of claim 1 wherein said inlet filling bulb is connected by said overflow tube to an outlet tube positioned below said measuring capillary tube.

3. In the flow-through capillary viscometer of claim 1 wherein the lower part of said inlet filling bulb is inclined downward and connected by an auxiliary capillary tube with said overflow tube.

4. In the flow-through capillary viscometer of claim 1 wherein a siphon, opening into said inlet filling bulb, is positioned above said inlet filling bulb.

5. In the flow-through capillary viscometer of claim 1 wherein a sample-thermostating chamber, opening into said inlet filling bulb, is positioned above said inlet filling bulb and is provided with a valve in the opening of said chamber into said inlet filling bulb.

6. In the flow-through capillary viscometer of claim 5 wherein said valve is connected with a rod controlled by an electromagnet.

7. The flow-through capillary viscometer of claim 1 wherein said viscometer is provided with photosensors.

* * * * *